United States Patent
Nagai et al.

(10) Patent No.: US 6,723,532 B2
(45) Date of Patent: *Apr. 20, 2004

(54) NEGATIVE STRAND RNA VIRAL VECTOR HAVING AUTONOMOUS REPLICATION CAPABILITY

(75) Inventors: Yoshiyuki Nagai, Tokyo (JP); Atsushi Kato, Tokyo (JP); Fukashi Murai, Ibaraki (JP); Makoto Asakawa, Ibaraki (JP); Tsuneaki Sakata, Osaka (JP); Mamoru Hasegawa, Ibaraki (JP); Tatsuo Shioda, Tokyo (JP)

(73) Assignee: Dnavec Research Inc., Ibaraki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 104 days.

(21) Appl. No.: 09/070,938

(22) Filed: Apr. 30, 1998

(65) Prior Publication Data

US 2002/0100066 A1 Jul. 25, 2002

Related U.S. Application Data

(63) Continuation of application No. PCT/JP96/03068, filed on Oct. 22, 1995.

(30) Foreign Application Priority Data

Oct. 31, 1995 (JP) .............................. 7/308315

(51) Int. Cl.[7] .................. C12N 15/00; C12N 15/63; C12N 5/00; C12N 5/06; C07H 21/02; C07H 21/04

(52) U.S. Cl. .................. 435/69.1; 435/320.1; 435/349; 435/325; 536/23.1

(58) Field of Search ................. 536/23.1; 424/93.1; 435/320.1, 325, 69.1, 455, 440, 91.1; 800/8

(56) References Cited

U.S. PATENT DOCUMENTS

| 5,166,057 A | 11/1992 | Palese et al. |
| 5,318,898 A | 6/1994 | Israeal |
| 5,578,473 A | 11/1996 | Palese et al. |
| 5,665,632 A | 9/1997 | Inglis et al. |
| 5,716,821 A | 2/1998 | Wertz et al. |
| 6,033,886 A | 3/2000 | Conzelmann ............ 435/172.3 |

FOREIGN PATENT DOCUMENTS

| EP | 0 440 219 A1 | 7/1991 |
| JP | 4-30791 | 2/1992 |
| JP | 5-85943 | 4/1993 |
| JP | 5-301895 | 11/1993 |
| WO | WO 94/08022 | 4/1994 |
| WO | WO96/10400 | 4/1996 |
| WO | WO 97/06270 | 2/1997 |
| WO | WO97/41245 | 11/1997 |

OTHER PUBLICATIONS

K–KConzelmann et al.,Journal of Virology, "Rescue of Synthetic Genomic RNA Analogs of Rabies Virus by Plasmid–Encoded Proteins," Feb. 1994, vol. 68, No. 2, pp. 713–719.*
Mullins JJ et al. Hypertension 22:630–633, 1993.*
Cameron ER. Molecular Biotechnology 7:253–265, 1997.*
Hammer RE et al. Cell 63:1099–1112.1990.*
Seidel GE. J. Anim. Sci. 71(Suppl. 3):26–33, 1993.*
Schnell et al. The EMBO Journal 13:4195–4203, 1994.*

(List continued on next page.)

*Primary Examiner*—Ram Shukla
(74) *Attorney, Agent, or Firm*—Chalin A. Smith; Smith Patent Consulting

(57) ABSTRACT

A method for reconstituting Sendai viral particles by transfecting Sendai virus to a host expressing all genes for the initial replication has been developed, enabling the Production of negative strand RNA vectors highly useful for practical applications.

11 Claims, 4 Drawing Sheets

OTHER PUBLICATIONS

Hassan et al J General Virology 78:2813–2820, 1997.*
Sakai et al FEBS Letters 456: 221–226, 1999.*
*Hahn, CS et al., Proc Natl Acad Sci USA, vol. 89(7):2679–83 (1992).
*Lawson, ND, et al., Proc Natl Acad Sci USA, vol. 92(18):8388–92 (1995).
Tokusumi, T. et al., Virus Research, vol. 86: 33–38 (2002).
*Whelan, SP et al., Proc Natl Acad Sci USA, vol. 89(7):4477–81 (1995).
M. Hamaguchi et al., "Transcriptive Complex of Newcastle Disease Virus," Virology 128: 105–117, 1983.
B. Gotoh et al., "An endoprotease homologous to the blood clotting factor X as a determinant of ciral tropism in chick embryo," EMBO J. 9: 4189–4195, 1990.
T. Shioda et al., "Determination of the complete nucleotide sequence of the Sendai virus genome RNA and the predicted amino acid sequences of the F, HN and L proteins," Nucleic Acids Res. 14: 1545–1563, 1986.
H. Kido et al., "Molecular basis of proteolytic activation of Sendai virus infection and the defensive compounds for infection," Biol. Chem. 378: 255–263, 1997.
J. K. Ghosh et al., "A leucine zipper motif in the ectodomain of Sendai virus fusion protein assembles in solution and in membranes and specifically binds biologically–active peptides and the virus," Biochemistry 36: 15451–15462, 1997.
A Kato et al., "Initiation of Sendai virus multiplication from transfected cDNA or RNA with negative or positive sense," Genes to Cells 1: 569–579, 1996.
A. Kato et al., "The paramyxovirus, Sendai virus, V protein encodes a luxury function required for viral pathogenesis," EMBO J. 16: 578–587, 1997.
A. Kato et al., "Importance of the cysteine–rich carboxyl––terminal half of V protein for Sendai virus pathogenesis," J. Virol. 71: 7266–7272, 1997.
M. Tashiro et al., "Importance of the mutated M protein in altered budding polarity of a pantropic mutant, F1–R, of Sendai virus," J. Virol. 70: 5990–5997, 1996.
J. Curran et al., "The Sendai virus P gene Expresses both an essential protein and an inhibitor of RNA synthesis by shuffling modules via mRNA editing," EMBO J. 10: 3079–3085, 1991.
J. Curran et al., "The hypervariable C–terminal tail of the Sendai paramyxovirus nucleocapsid protein is required for template function but not for RNA Encapsidation," J. Virol 67: 4358–4364, 1993.
D. Garcin et al., "A highly recombinogenic system for the recovery of infectious Sendai paramyxovirus from cDNA: generation of a novel copy–back nondefective interfering virus," EMBO J. 14: 6087–6094, 1995.
C. Delenda et al., "Normal cellular replication of Sendai virus without the trans–frame, nonstructural V protein," Virology 228: 55–62, 1997.
D. Garcin et al., "A point mutation in the Sendai virus accessory C proteins attenuates virulence for mice, but not virus growth in cell culture," Virology 238: 424–431, 1997.
C. Tapparel et al., "Inhibition of Sendai virus genome replication due to promoter–increased selectivity: a possible role for the accessory C proteins," J. Virol. 71: 9588–9599, 1997.
K. H. Park et al., "Rescue of a foreign gene by Sendai virus," Proc. Natl. Acad. Sci. USA 88: 5537–5541, 1991.

K. H. Park et al., "In vivo model for pseudo–templated transcription in Sendai virus," J. Virol. 66: 7033–7039, 1992.
P. Calain et al., "The rule of six, a basic feature for efficient replication of Sendai virus defective interfering RNA," J. Virol 67: 4822–4830, 1993.
P. Calain et al., "Molecular cloning of natural paramyxovirus copy–back defective interfering RNAs and their expression from DNA," Virology 191: 62–71, 1992.
P. Calain et al., "Functional characterisation of the genomic and antigenomic promoters of Sendai virus" Virology 212: 163–173, 1995.
G. Mottet et al., "A Sendai virus vector leading to the efficient expression of mutant M proteins interfering with virus particle budding" Virology 221: 159–171, 1996.
F. Radecke et al., "The nonstructural C protein is not essential for multiplication of edmonston B strain measles virus in cultured cells" Virology 217: 418–421, 1996.
V.M. Hill et al., "A minor microtubule–associated protein is responsible for the stimulation of vesicular stomatitis virus transcription in vitro" J. General Virology 71: 289–298, 1990
K. Mizumoto et al., "Protein factors required for in vitro transcription of Sendai virus genome" J. Biochem. 117: 527–534, 1995.
T. Takagi et al., "In vitro mRNA synthesis by Sendai virus: isolation and characterization of the transcription initiation complex" J. Biochem. 118: 390–396, 1995.
S. A. Moyer et al., "Tubulin: A factor necessary for the synthesis of both Sendai virus and vesicular stomatitis virus RNAs" Proc. Natl. Acad. Sci. USA 83: 5405–5409, 1986.
R. Chandrika et al., "Mutations in conserved domain I of the Sendai virus L polymerase protein uncouple transcription and replication" Virology 213: 352–363, 1995.
S. M. Horikami et al., "The Sendai virus C protein binds the L polymerase protein to inhibit viral RNA synthesis" Virology 235: 261–270, 1997.
W. J. Neubert et al., "Transient rescue of Sendai–6/94 cl virus from the persistently infected cell line CI–E–8 by cocultivation" Virology 125: 445–453, 1983.
M. Sigmund et al., "Simple method for rapid and highly sensitive detection of antiviral–antibodies in serum and cerebrospinal fluid of small laboratory animals" Journal of Virological Methods 22: 231–238, 1988.
H. Einberger et al., "Purification, renaturation, and reconstituted protein kinase activity of the Sendai virus large (L) protein: L protein phosphorylates the NP and P proteins in vitro" J. Virol. 64: 4274–4280, 1990.
H. E. Homann et al., "Sendai virus gene expression in lytically and persistently infected cells" Virology 177: 131–140, 1990.
H. E. Homann et al., "Sendai Virus protein–protein interactions studied by a protein–blotting protein–overlay technique: mapping of domains on NP protein required for binding to P protein" J. Virol. 65: 1304–1309, 1991.
W. Willenbrink et al., "Long–term replication of Sendai virus defective interfering particle nucleocapsids in stable helper cell lines" J. Virol. 668: 8413–8417, 1994.
C.J. Buchholz et al., "The conserved N–terminal region of Sendai virus nucleocapsid protein NP is required for nucleocapsid assembly" J. Virol. 67: 5803–5812, 1993.

P.L.. Collins et al., "Rescue of synthetic analogs of respiratory syncytial virus genomic RNA and effect of truncations and mutations on the expression of a foreign reporter gene" Proc. Natl. Acad. Sci. USA 88: 9663–9667, 1991.

P.L.. Collins et al., "production of infectious human repiratory syncytial virus from cloned cDNA confirms an essential role for the transcription elongation factor from the 5' proximal open reading frame capability for vaccine deleloment" Proc. Natl. Acad. Sci. USA 92: 11563–11567, 1995.

A. P Durbin et al., "Recovery of infection human parainfluenza type 3 from cDNA" Virology 235: 323–332, 1997.

A. P. Durbin et al., "Minimum protein requirements for transcription and RNA replicationof a minigenome of human parainfluenza virus type 3 and evaluation of the rule of six" Virology 234: 74–83, 1997.

A. Bukreyev et al., "Recombinant respiratory syncytial virus from which the entire SH gene has been deleted grows efficiently in cell culture and exhibits site–specific attenuation in the respiratory tract of the mouse" J. Virol. 71:8973–8982, 1997.

K.–K. Conzelmann et al., "Genetic engineering of animal RNA viruses" Trends in Microbiology 4:386–393 1996.

M. J. Schnell et al., "Infections rabies viruses from cloned cDNA" EMBO J. 13: 4195–4203, 1994.

K. Tanabayashi et al., "Functional interaction of paramyxovirus glycoproteins: Identification of a domain in sendai virus HN which promotes cell fusion" J. Virol. 70: 6112–6118, 1996.

L. S. Tsimring et al., "RNA virus evolution via a fitness–space model" Physical Review Letters 76: 4440–4443, 1996.

E. Domingo et al., "Basic concepts in RNA virus evolution" FASEB J. 10, 859–864, 1996.

P. Palese, "Genetic engineering of infectious negative–strand RNA viruses" Trends in Microbiology 3: 123–125, 1995.

P. Palese et al., "Negative–strand RNA viruses: Genetic engineering and applications" Proc. Natl. Acad. Sci. USA 93: 11354–11358, 1996.

T. Sakaguchi et al., "Expression of the HN, F, NP and M proteins of Sendai virus by recombinant vaccinia viruses and their contribution to protective immunity against sendai virus infections in mice" J. General Virology 74: 479–484, 1993.

J. L. Hurwitz et al., "Intranasal sendai virus vaccine protects African green monkeys from infection with human parainfluenza virus–type one" Vaccine 15: 533–540, 1997.

C. J. Buccholz et al., "The caboxy–terminal domain of sendai virus nucleocapsid protein is involved in complex formation between phosphoprotein and nucleocapsid–like partickes" Virology 204: 770–776, 1994.

K. C. Gupta et al., "Lack of correlation between sendai virus P/C mRNA structure and its utilization of two AUG start sites from alternate reading frames: Implications for viral bicistronic mRNAS" Biochemistry 35: 1223–1231, 1996.

B.P. De et al., "Rescue of synthetic analogs of genome RNA of human parainfluenza virus type3" Virology 196: 344–348, 1993.

P. Latorre et al., "The various sendai virus C proteins are not functionally equivalent and exert both positive and negative effects on viral RNA accumulation during the course of infection" J. Virol. 72: 5984–5993, 1998.

K.–K. Conzelmann, "Genetic manipulation of non–segmented negative–strand RNA viruses" J. General Virology 77: 381–389, 1996.

B. P. De et al., "Reverse genetics of negative strand RNA viruses" Indian Journal of Biochemistry & Biophysics 31: 367–376, 1994.

T. Tao et al., "Host range restriction of parainfluenza virus growth occurs at the level of virus genome replication" Virology 220: 69–77, 1996.

D. S. Lyles et al., "Complementation of M gene mutants of vesicular stomatitis virus plasmid–derived M protein converts spherical extracellular particles into native bullets shapes" Virology 217: 76–87, 1996.

A. Bridgen et al., "Rescue of a segmented negative–strand RNA virus entirely from cloned complementary DNAs" Proc. Natl. Acad. Sci. USA 93: 15400–15404, 1996.

M. M. Rolls et al., "Expression of additional genes in a vector derived from a minimal RNA virus" Virology 218: 406–411, 1996.

H. Kido et al., "Molecular basis of proteolytic activation of Sendai virus infection and defensive compounds for infection" Biol. Chem. 378: 255–263, 1997.

Garcia–Sastre, A. et al., Ann. Rev. Microbiol. 47:765–90 (1993).

Gotoh, H. et al., Virology 171(2):434–43 (1989).

Kondo, T. et al., J. Biol. Chem. 268(29):21924–30 (1993).

Luytjes, W. et al., Cell 59:1107–1113 (1989).

Malinoski, F. et al., Virology 110:281–291 (1981).

Metsikko, K. et al., J. Virology 63(12): 5111–5118 (1989).

Nakanishi, M. et al., J. Cell. Biochem, Suppl (21A) C6–337 (1995) –Abstract only.

Peavy, D. et al., J. Immunol. 126(3): 861–864 (1981).

Pekosz, A. et al., PNAS USA 96:8804–8806 (Aug., 1999).

Stricker, R. et al., J. Gen. Virol. 75:1031–1042 (1994).

Toriyoshi, H. et al., Aids Res. & Human Retroviruses 15(12): 1109–1120.

Tuffereau, C. et al., Virology 162:417–426 (1988).

Yonemitsu, Y. et al., Surgery 131(1): S261–268 (Jan., 2002).

* cited by examiner

A. Using a cell line expressing the NP, P, L, and M proteins as the packaging cell, viral RNA is transcribed from cDNA deficient in the M gene, and one type of viral particles deficient in the M gene (△M type viral particles) is eventually produced.

B. These △M type viral particles can be amplified in M gene expressing cells and recovered in a high titer.

C. Normal cells are infected with △M type viral particles, wherein the viral RNA is replicated within the cells, but viral particles are not formed.

ized to insert a desired gene are associated the nucleocapsid and envelope proteins, etc. which are derived from the parental virus and confer infectivity on the recombinant virus. These proteins enable the transfer of the enclosed recombinant gene into cells. Such recombinant viral vectors can be used for the purpose of not only gene therapy, but also production of cells expressing a desired gene as well as transgenic animals.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:1:

TGCGGCCGCC GTACGGTGGC AATGAGTGAA GGAGAAGT      38

(2) INFORMATION FOR SEQ ID NO:2:

(i) SEQUENCE CHARACTERISTICS:
      (A) LENGTH: 69 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:2:

TTGCGGCCGC GATGAACTTT CACCCTAAGT TTTTVTTACT ACGGCGTACG TCATCTTTTT      60

TCTCTCTGC      69

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:3:

AAGCGGCCGC CAAAGTTCAC GATGGAAGAC      30

(2) INFORMATION FOR SEQ ID NO:4:

(i) SEQUENCE CHARACTERISTICS:
      (A) LENGTH: 68 base pairs

-continued

```
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

TGCGGCCGCG ATGAACTTTC ACCTAAGTTT TTCTTACTAC GGATTATTAC AATTTGGACT        60

TTCCGCCC                                                                68
```

NEGATIVE STRAND RNA VIRAL VECTOR HAVING AUTONOMOUS REPLICATION CAPABILITY This application is a continuation of PCT International Application No. PCT/JP96/03068, filed Oct. 22, 1996, which, in turn, claims the benefit of Japanese Patent Application No. 7/308,315, filed Oct. 31, 1995.

FIELD OF THE INVENTION

The present invention relates to a viral vector for the gene therapy. More specifically, this invention relates to a negative strand RNA viral vector.

BACKGROUND OF THE INVENTION

As to the gene therapy for humans and animals, therapeutic effectiveness and safety are very important factors. Especially, therapy performed by using "viral vector" expressing a foreign gene of concern which is obtained by gene recombination of the viral genome and the foreign gene needs to be very cautiously carried out, when such undeniable possibilities exist as that the recombinant virus may be inserted to unspecified sites of chromosomal DNA, that the recombinant virus and pathogenic virus may be released to the natural environment, and that the expression level of gene transfected into cells cannot be controlled, or the like, even though its therapeutic effectiveness is recognized.

These days, a great number of gene therapies using recombinant viruses are performed, and many clinical protocols of gene therapy are proposed. Characteristics of these recombinant viral vectors largely depend on those of the viruses from which said vectors are derived. The basic principle of viral vector is a method for transferring the desired gene into targeted cells by utilizing the viral infectivity. By "infectivity" in this specification is meant the "capability of a virus to transfer its nucleic acid, etc. into cells through its adhesiveness to cells and penetrating capability into cells via various mechanisms including fusion of the viral membrane and host cellular membrane". With the surface of recombinant viral vectors genetically manipulated to insert a desired gene are associated the nucleocapsid and envelope proteins, etc. which are derived from the parental virus and confer infectivity on the recombinant virus. These proteins enable the transfer of the enclosed recombinant gene into cells. Such recombinant viral vectors can be used for the purpose of not only gene therapy, but also production of cells expressing a desired gene as well as transgenic animals.

Viral vectors are classified into three classes comprising the retroviral vector, DNA viral vector and RNA viral vector.

These days, the vectors most frequently used in gene therapy are retroviral vectors derived from retroviruses. Retroviruses replicate through the following processes. First, upon penetration into cells, they generate complementary DNAs (cDNAs) using their own reverse transcriptase as at least part of catalysts and their own RNA templates. After several steps, said cDNAs are incorporated into host chromosomal DNAs, becoming the proviruses. Proviruses are transcribed by the DNA-dependent RNA polymerase derived from the host, generating viral RNAs, which is packaged by the gene products (proteins) translated from the RNAs. The RNAs and proteins finally assemble to form mature virus particles.

In general, retroviral vectors used in gene therapy, etc. are capable of carrying out processes up to provirus generation. However, they are deficient viruses deprived of genes necessary for their packaging of the progeny genome RNA so that they do not form viral particles from provirus. Retroviruses are exemplified by, for example, mouse leukemia virus, feline leukemia virus, baboon type C oncovirus, human immunodeficiency virus, adult T cell leukemia virus, etc. Furthermore, recombinant retroviral vectors hitherto reported include those derived from mouse leukemia virus [see Virology, 65, 1202 (1991), Biotechniques, 9, 980 (1989), Nucleic Acids Research, 18, 3587 (1990), Molecular and Cellular Biology, 7, 887 (1987), Proceedings of National Academy of Sciences of United States of America, 90, 3539 (1993), Proceedings of National Academy of Sciences of United States of America, 86, 3519 (1989), etc.] and those derived from human immunodeficiency virus [see Journal of Clinical Investigation, 88, 1043 (1991)], etc.

Retroviral vectors are produced aiming at efficiently inserting a desired specific DNA into the cellular chromosomal DNA. However, since the insertion position of the DNA is unpredictable, there is undeniable possibilities such as the damage of normal genes, activation of oncogene and excessive or suppressive expression of desired gene, depending the position of insertion. In order to solve these problems, a transient expression system using DNA viral vectors which can be used as extrachromosomal genes has been developed.

DNA viral vectors are derived from DNA viruses, having DNA as genetic information within viral particles. Replication of said DNA is carried out by repeating the process of generating complementary DNA strand using DNA-dependent DNA replicase derived from host as at least one of catalysts with its own DNA as template. The actual gene therapy using adenoviral vector, a DNA viral vector usable as extrachromosomal gene, is exemplified by the article in [Nature Genetics, 3, 1-2 (1993)]. However, since, in the case of DNA viral vectors, the occurrence of their undesirable recombination with chromosomal DNA within nucleus is also highly possible, they should be very carefully applied as vectors for gene therapy.

Recently, RNA viral vectors based on RNA viruses have been developed as conceivably more safer vectors than DNA and retroviral vectors described above. RNA viruses replicate by repeating the processes for generating complementary strands using their own RNA-dependent RNA replicase as the catalyst with their own RNA as template.

The genome RNA of positive strand RNA viruses have dual functions as the messenger RNA (hereafter simply called mRNA), which generate proteins, depending on the translational functions of host cells, necessary for the replication and viral particle formation and as the template for genome replication. In other words, the genome RNA itself of positive strand RNA viruses has a disseminative capability. In the present specification, by "disseminative capability" is meant "the capability to form infectious particles or their equivalent complexes and disseminate them to other cells following the transfer of nucleic acid into host cells by infection or artificial techniques and the intracellular replication of said nucleic acid". Sindbis virus classified to positive strand RNA viruses and Sendai virus classified to negative strand RNA viruses have both infectivity and disseminative capability. Adeno-satellite virus classified in Parboviruses is infectious but not disseminative (mixed infection with adenovirus is required for the formation of viral particles.). Furthermore, the positive strand RNA derived from Sindbis virus which is artificially transcribed in vitro is disseminative (forming infectious viral particles when transfected into cells), but neither positive nor negative RNA strands of Sendai virus artificially transcribed in vitro is disseminative, generating no infectious viral particles when transfected into cells.

In view of the advantage that the genome RNA functions as mRNA at the same time, the development of RNA viral vectors derived from positive strand RNA viruses preceded [see Bio/Technology, 11, 916–920 (1993), Nucleic Acids Research, 23, 1495–1501 (1995), Human Gene Therapy, 6, 1161–1167 (1995), Methods in Cell Biology, 43, 43–53 (1994), Methods in Cell Biology, 43, 55–78 (1994)]. For example, RNA viral vectors derived from Semliki forest virus (SFV) [Bio/Technology, 11, 916–920 (1993)] and Sindbis virus are basically of the RNA structure wherein the structural protein gene regions related to the viral structure are deleted, and a group of genes encoding proteins necessary for viral transcription and replication are retained with a desired foreign gene being linked downstream of the transcription promotor. Direct transfer of such recombinant RNA or cDNA which can transcribe said RNA [Nucleic Acids Research, 23, 1495–1501 (1995)] into cells by microinjection, etc. allows autonomous replication of RNA vectors containing the foreign gene, and the transcription of foreign gene inserted downstream of the transcription promotor, resulting in the expression of the desired products from the foreign gene within cells. Furthermore, the present inventors succeeded in forming an infectious but not disseminative complex by the co-presence of cDNA unit (helper) for expressing the viral structural gene and that for expressing said RNA vector in the packaging cells.

Positive strand RNA viral vectors are expected to be useful as RNA vectors with autonomous replicating capability, but their use as vectors for gene therapy poses the following problems.

1. Since they are of the icosohedral structure, the size of foreign gene allowed to be inserted is limited to 3,700 nucleotides at most.

2. Until nucleic acids are released from the packaged complex into the cell and replicated, as many as five processes are required, including cellular adhesion, endocytosis, membrane fusion, decapsidation and translation of replication enzymes.

3. A possible formation of disseminative viral particles even in a minute quantity during packaging cannot be denied. Especially, even with attenuated viral particles, the inside RNA itself has disseminative potency and may belatedly be amplified, making it difficult to check.

4. Since these vectors are derived from viruses transmitted to animals by insects such as mosquitoes, when animals and humans to which such vector genes are transferred and are mix-infected with wild type viruses, disseminative recombinants may be formed, possibly further creating a risk of said recombinants being scattered to the natural environment by insects.

Such problems described above are conceived to be basically overcome if RNA viral vectors derived from negative strand RNA viruses are constructed. That is, since negative strand RNA viruses do not have the capsid of icosohedral structure but have a helical nucleocapsid, and also since the envelope size of particles is known to vary depending on the inside RNA content, they are supposed to be much less restricted, compared with positive strand RNA viruses, with respect to the size of foreign genes to be inserted when used as RNA viral vectors. Further, since a group of proteins required for transcription and replication are packaged into particles, only two processes are required, including cellular adhesion and membrane fusion, until nucleic acids are replicated. Furthermore, viral RNA alone is not disseminative. In addition, most of negative strand RNA viruses are not transmitted by insects.

In spite of many advantages of negative strand RNA viruses which may be used as the source of industrially useful viral vectors, no negative strand RNA vectors applicable for gene therapy has become available until now. This is probably due to tremendous difficulties in re-constituting viral particles via viral cDNA. Since the gene manipulation on the DNA level is required to insert foreign genes into vectors, so far as viral particles are not reconstructed from viral cDNA with a foreign gene inserted, it is difficult to use negative strand RNA viruses as a vector. "Reconstruction of viral particles" refers to the formation of the original virus or a recombinant virus in vitro or intracellularly from artificially prepared cDNA encoding the viral RNA genome.

As described above, it has been clearly demonstrated that, even if the viral RNA (vRNA) of negative strand RNA viruses or its complementary strand RNA (cRNA; complementary RNA) alone is transferred into cells, no progeny virus can be generated. This is a definitely different point from the case of positive strand RNA viruses, whose RNA can initiate viral life cycle and generate progeny viruses, when transferred into cells. Although, in JP-A-Hei 4-211377, "methods for preparing cDNA corresponding to a nonsegmented negative strand RNA viral genome and infectious negative strand RNA virus" are described for measles virus, a paramyxovirus, the entire experiments of said document described in "EMBO. J., 9, 379–384 (1990)" were later proved to be not reproducible, so that the authors themselves had to withdrew all the article contents [ref. EMBO. J., 10, 3558 (1991)]. Therefore, it is obvious that techniques described in JP-A-Hei 4-211377 for another paramyxovirus, Sendai virus, do not correspond to the related art of the present invention.

With regard to the reconstitution system for negative strand RNA viruses, there are reports on influenza virus [Annu. Rev. Microbiol., 47, 765–790 (1993); Curr. Opin. Genet. Dev., 2, 77–81 (1992)]. Influenza virus is an eight-segmented negative strand RNA virus. According to these literatures, a foreign gene was first inserted to a cDNA corresponding to one of said segments, and the RNA transcribed from the cDNAs is assembled with the virus-derived NP protein and RNA polymerase proteins to form an RNP. Then, cells are transfected with this RNP and superinfected with an appropriate intact influenza virus. A reassortant virus emerges, in which the corresponding segment is replaced with the engineered segment, which can be selected under apporopriate pressures. Several years later, virus-reconstitution entirely from cDNA of nonsegmented negative strand RNA virus was reported with rabies virus belonging to rhabdoviruses [EMBO J. 13, 4195–4202 (1994)].

However, it has been difficult to use these virus reconstitution techniques as such for constructing vectors for gene therapy because of the following problems.

1. Reconstituted viruses were identified only by the expression of marker gene, RT-PCR, etc. No re-constitution system for the production of vector viruses in a satisfactory yield has been established.

2. Differing from the case of positive strand RNA viruses, in order to form complexes with infectivity but deficient in disseminative potency as vectors for gene therapy, it is necessary to enclose factors required for primary transcription and replication within the complex. No technique for amplifying these complexes in a large scale has been established.

3. For the purpose of intracellularly providing factors necessary for viral reconstitution, cells to which cDNAs are introduced are mix-infected with helper viruses such as recombinant vaccinia virus, etc. to allow transcription of the plasmids supplying those viral protein factors in trans. It is not easy to separate these natural type viruses from the recomstituted viruses.

Furthermore, as one problem with regard to RNA viral vectors in general, it is conceivably necessary to beforehand provide inhibitors for replication of RNA viral vectors which have no effects on host's replication and transcription, providing for the case where RNA replicated and transcribed in large amounts exerts undesirable effects on treated humans and animals. However, no such inhibitors have been developed.

SUMMARY OF THE INVENTION

Objects of the present invention are to develop negative strand RNA viral vectors for practical use, methods for efficiently preparing said vectors, and inhibitors for the replication of said vectors.

The present inventors first attempted to reconstitute Sendai virus from nucleic acids of said virus which is a typical nonsegmented, negative strand RNA virus, and conceived to be industrially most useful as a vector from the viewpoints of safety and convenience. First, in order to apply to the reconstitution test, various investigations were performed using cDNA encoding a Sendai virus minigenome as experimental materials. A cDNA plasmid was constructed so that the Sendai virus protein coding region of about 14 kb is replaced with a reporter luciferase gene and this construct is flanked by T7 promoter and hepatitis delta virus ribozyme gene. As a result, the inventors found efficient conditions regarding weight ratios among materials to be transferred into host cells, including minigenome cDNA, cDNAs encoding the nucleocapsid protein (N), the large protein (L), and the phosphoprotein (P), and minimizing cytotoxicity induced by the recombinant vaccinia virus to provide the T7RNA polymerase. The N protein encapsidate the naked viral RNA to form the RNP, which is now active as the template for both viral mRNA synthesis and viral replication. Furthermore, the present inventors obtained full-length cDNAs corresponding to both positive and negative strands, constructed plasmids for inducing the intracellular biosynthesis of either positive strand RNA (antigenome or cRNA) or negative strand RNA (genome or vRNA) of Sendai virus, and transferred said plasmids into host cells wherein N, P, and L proteins from the respective cotransfected plasmids were expressed. As a result, the inventors first succeeded in re-constructing Sendai virus particles from cDNAs derived thereof.

That is, the present invention comprises the followings.

1. A complex comprising an RNA molecule derived from a specific disseminative negative strand RNA virus and viral structural components containing no nucleic acids, having the infectivity and autonomous RNA replicating capability, but deficient in the disseminative capability.

2. The complex of description 1, wherein said specific RNA virus is a negative strand RNA virus having non-segmented genome.

3. The complex of description 2, wherein said specific RNA virus is Sendai virus.

4. An RNA molecule comprising Sendai viral RNA (vRNA) or its complementary RNA (cRNA), wherein said RNA molecule is defective in that at least one or more than one gene coding for each of the M, F and HN proteins are deleted or inactivated.

5. A complex comprising the RNA of description 4 and viral structural components containing no nucleic acids derived from Sendai virus, having the infectivity and autonomous RNA replicating capability, but deficient in the disseminative capability.

6. A DNA molecule comprising a template DNA transcribable to the RNA molecule of description 4 in vitro or intracellularly.

7. The complex of any one of descriptions 1–3 or 5, wherein the RNA molecule contained in said complex comprises a foreign gene.

8. The complex of descriptions 3 or 5, wherein the RNA molecule contained in said complex comprises a foreign gene.

9. The RNA molecule of description 4 comprising a foreign gene.

10. The DNA molecule of description 6 comprising a foreign gene.

11. An inhibitor for RNA replication contained in the complex of any one of descriptions 1–3, 5, 7 or 8 comprising an inhibitory drug for the RNA-dependent RNA replication.

12. A host whereto the complex of any one of descriptions 1–3, 5, 7 or 8 can disseminate.

13. The host of description 12 comprising a group of genes related to the infectivity of the complex of any one of descriptions 1–3, 5, 7 or 8 on its chromosomes, and capable of replicating the same copies of said complex when infected with it.

14. The host of descriptions 12 or 13, wherein said host is animals, or cells, tissues, or embryonated eggs derived from it.

15. The host of description 14 wherein said animal is mammalian.

16. The host of description 14 wherein said animal is avian.

17. A host comprising a group of genes related to the infectivity of the complex of any one of descriptions 3, 5 or 8 on its chromosomes, and capable of replicating the same copies of said complex when infected with it.

18. A host comprising at least more than one gene of the M, F and HN genes of Sendai virus or genes having functions equivalent to them on its chromosomes.

19. A host comprising the M, F, or HN gene of Sendai virus or each of their functionally equivalent genes on its chromosomes.

20. A host comprising the M, NP, P and L genes of Sendai virus on its chromosomes (wherein each gene may be substituted with its functionally equivalent gene, respectively).

21. A host comprising the M, F and HN genes of Sendai virus on its chromosomes (wherein each gene may be substituted with its functionally equivalent gene, respectively).

22. A host comprising the M, F, HN, NP, P and L genes of Sendai virus on its chromosomes (wherein each gene may be substituted with its functionally equivalent gene, respectively).

23. The host of any one of descriptions 17–22, wherein said host is animal, or cell, tissue or egg derived from it.

24. The host of description 23, wherein said animal is mammalian.

25. The host of description 23, wherein said animal is avian.

26. A kit consisting of the following three components,
    a. the RNA molecule contained in the complex of any one of descriptions 1–3, 5, 7 or 8, or cRNA of said RNA, or a unit capable of biosynthesizing said RNA or said cRNA,
    b. a group of enzymes required for replicating said RNA or said cRNA, or a unit capable of biosynthesizing said group of enzymes, and
    c. a group of proteins related to the infectivity of said complex, or a unit for biosynthesizing said group of proteins.

27. A kit consisting of the following three components,
    a. the RNA molecule contained in the complex of any one of descriptions 1–3, 5, 7 or 8, or cRNA of said RNA, or a unit capable of biosynthesizing said RNA or said cRNA,
    b. a group of enzymes required for replicating said RNA or said cRNA, or a unit capable of biosynthesizing said group of enzymes, and
    c. the host of any one of descriptions 12–25.

28. A kit consisting of the following two components,
    a. the complex of any one of descriptions 1–3, 5, 7 or 8, and
    b. the host of any one of descriptions 12–25.

29. A kit consisting of the following three components,
    a. the RNA molecule contained in the complex of any one of descriptions 3, 5 or 8, or cRNA of said RNA, or a unit capable of biosynthesizing said RNA or said cRNA,
    b. all NP, P and L proteins of Sendai virus, or a unit for biosynthesizing said group of proteins, and
    c. a group of proteins related to the infectivity of said complex, or a unit for biosynthesizing said group of proteins.

30. A kit consisting of the following three components,
    a. the RNA molecule contained in the complex of any one of descriptions 3, 5 or 8, cRNA of said RNA, or a unit capable of biosynthesizing said RNA or said cRNA,
    b. all NP, P and L proteins of Sendai virus, or a unit capable of biosynthesizing said group of proteins, and
    c. the host of any one of descriptions 17–25.

31. A kit consisting of the following two components,
    a. the complex of any one of descriptions 3, 5 or 8, and
    b. the host of any one of descriptions 17–25.

32. A method for producing the complex of any one of descriptions 1–3, 5, 7 or 8 by introducing three components of descriptions 26a, 26b and 26c into a host.

33. A method for producing the complex of any one of descriptions 1–3, 5, 7 or 8 by introducing both components of descriptions 27a and 27b into the host of description 27c.

34. A method for amplifying and producing the complex of description 28a by transfecting said complex to the host of description 28b.

35. A method for producing the complex of any one of descriptions 3, 5 or 8 by introducing the three components of descriptions 29a, 29b and 29c into a host.

36. A method for producing the complex of any one of descriptions 3, 5 or 8 by introducing both components of descriptions 30a and 30b into the host of description 30c.

37. A method for amplifying and producing the complex of description 31a by transfecting said complex into the host of description 31b.

38. The RNA molecule of description 9 wherein a gene corresponding to the M, F, or HN gene is deleted or inactivated.

39. The RNA molecule of description 9 wherein all the genes corresponding to the M, F and HN genes are deleted or inactivated.

40. A kit consisting of the following three components,
    a. the RNA molecule of description 38,
    b. the host of description 20, and
    c. the host of description 19.

41. A method for producing a complex by introducing the RNA molecule of description 40a into the host of description 40b, and amplifying and producing said complex by transfecting it into the host of description 40c.

42. A complex produced by the method of description 41.

43. A kit consisting of the following three components,
    a. the RNA molecule of description 39,
    b. the host of description 22, and
    c. the host of description 21.

44. A method for producing a complex by introducing the RNA molecule of description 43a into the host of description 43b, and amplifying and producing said complex by transfecting it into the host of description 43c.

45. A complex produced by the method of description 44.

46. An inhibitor for RNA replication contained in the complex of either descriptions 42 or 45 comprising an inhibitory drug of the RNA-dependent RNA replication.

47. A method for preparing the foreign proteins, wherein said method comprises the process of introducing the complex of description 7 to a host and the process of recovering the expressed foreign proteins.

48. A method for preparing the foreign proteins of description 47, wherein the host is a cell expressing a group of genes, from among those related to the disseminative capability, which are deficient in the RNA molecule contained in the complex of description 7.

49. A culture medium or allantoic fluid containing the expressed foreign proteins, wherein said culture medium or allantoic fluid is obtained by inoculating the complex of description 7 into a host and recovering it.

DETAILED DESCRIPTIN OF THE INVENTION

Figure 1:
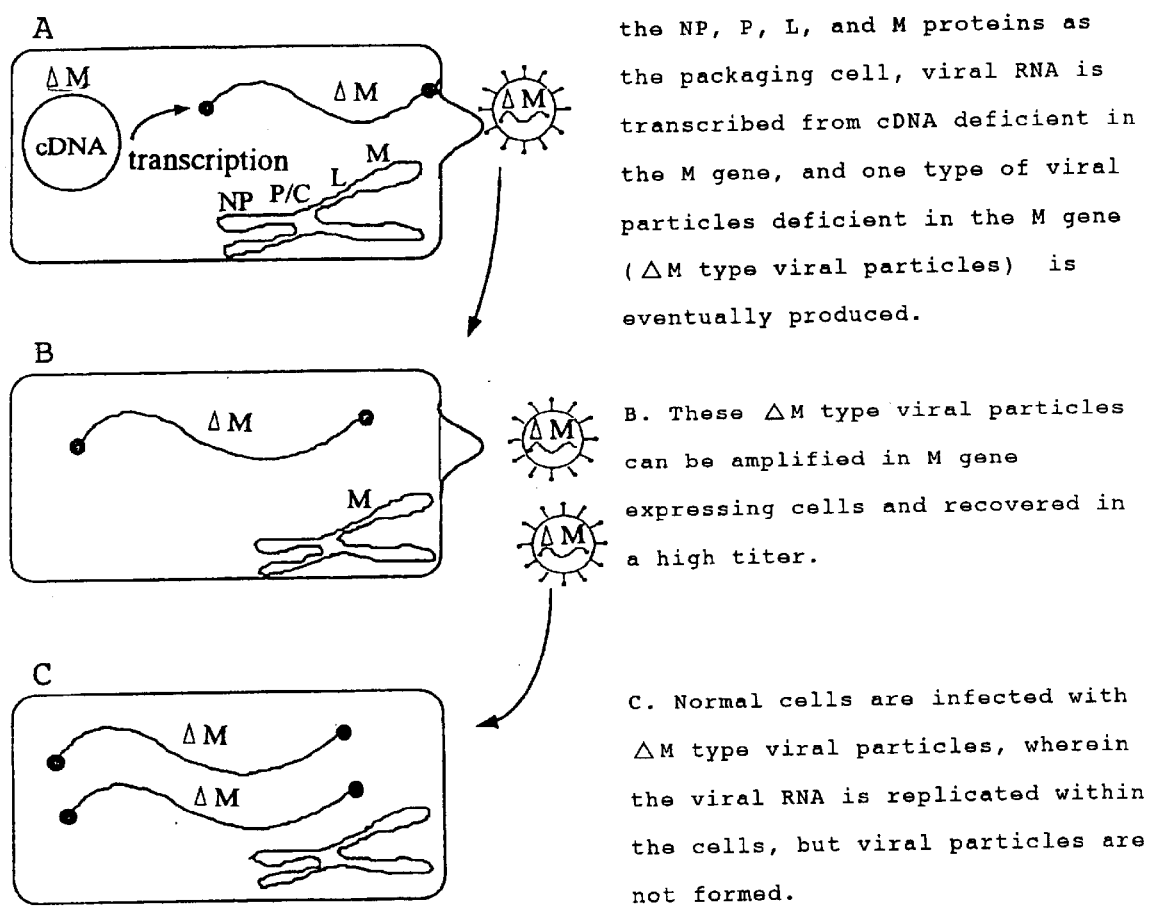
FIGS. 1A–C is a schematic representation of a process for generating complexes of the present invention from cDNA deficient in the M gene of Sendai virus (step A) amplifying said complexes in an M-expressing cell (step B), and replication of said complexes in a normal cell (step C).

Any negative strand RNA viruses with disseminative capability may be used as materials in the present invention. Although incomplete viruses such as defective interfering particles (DI particles) and synthetic oligonucleotide may also be used as partial materials, in general, they must have the base sequence equivalent to that of the virus with disseminative capability. Negative strand RNA viruses of the present invention include, for example, Sendai virus, Newcastle disease virus, mumps virus, measles virus, respiratory syncytial virus, rinderpest virus of cattle and canine distemper virus of Paramyxoviridae, influenza virus of Orthomyxoviridae, vesicular stomatitis virus and rabies virus of Rhabdoviridae.

As the negative strand viral material, recombinant negative strand viruses derived from any viruses described above and retaining the disseminative capability may be used. For example, the recombinant negative strand virus may be the one with the gene for the immunogenicity inactivated or a partial region of gene altered to enhance the efficiency of RNA transcription and replication.

RNAs contained in the RNA-protein complex of the present invention can be obtained by transcribing modified cDNAs derived from any viruses or recombinant viruses described above in vitro or intracellularly. In RNAs thus obtained, at least one gene related to the disseminative capability of the original virus must be deleted or inactivated, but the gene related to the autonomous replication should not. In addition, RNA molecules with artificial sequences, which are obtained by transcribing, in vitro or intracellularly, DNA formed by inserting the genes for the autonomous replication into cDNA having both terminus structures of the virus genome may be also used.

As described above, in the case of Sendai virus, "the genes related to autonomous replication" refer to the NP, P and L genes, and "the gene related to the disseminative capability" refers to any one of the M, F and HN genes. Therefore, the RNA molecule of Sendai virus Z strain deficient only in the M gene, for example, is suitable as a component contained in the "complex" of the present invention. Also, the RNA molecule having all the M, F and HN genes deleted or inactivated are also preferable as the component contained in the "complex" of the present invention. On the other hand, it is necessary for the genes encoding the NP, P and L proteins to be expressed from RNA. However, the sequences of these genes are not necessarily the same as those of virus, and may be modified by introducing variations, or replacing by the corresponding gene derived from other viruses, so far as the transcription and replication activity of the resulting RNA is similar to or higher than that of the natural one.

"Virus structural component free of nucleic acid" of the present invention includes, for example, virus with only its RNA removed. As such structural component is used the one which complements the infectivity and autonomous replicating capability at the early stage, but not the disseminative capability. In the case of Sendai virus, the complex composed of its RNA with only the M gene deleted, and Sendai virus having only its RNA deleted have the infectivity and autonomous replicating capability, but no disseminative capability. Complex may contain other components so long as it is provided with no disseminative capability. For example, complex may contain adhering molecule, ligand, receptors, etc. on its envelope surface for facilitating the adherence to specific cells.

The RNA molecule contained in the complex can have an inserted foreign gene at its appropriate site. In order to express a desired protein, the foreign gene encoding said protein is inserted. In the case of Sendai viral RNA, a sequence of bases of 6 multiplication in number is preferably inserted between sequences R1 (5'-AGGGTCAAAGT-3') (SEQ ID NO:5) and R2 (5'-GTAAGAAAAA-3')(SEQ ID NO:6) [Journal of Virology, Vol. 67, No. 8. (1993), p. 4822–4830]. Levels of expression of the foreign gene inserted into RNA can be regulated by virtue of the site of gene insertion and the base sequence flanking the inserted foreign gene. For example, in the case of Sendai viral RNA, it is thought that there are increasing levels of expression of the inserted gene with decreasing distance of said gene from the 3' terminal promoter, whose length has not been precisely defined yet. Preferred host cells for the introduction of the complex to express in high quantities desired proteins are those expressing genes deleted in the RNA molecule composed of said complex. For this, transgenic avian eggs expressing said genes are most preferable for preparing proteins in large quantities because said genes complement the defects of the virus, facilitating the virus production and thus yielding the inserted gene product in high quantities in the allantoic fluid. Also, proteins thus expressed can be recovered from the culture medium when the avian cells are cultured in vitro. In Examples 5 and 6 is used a disseminative complex in place of non-disseminative complex of the present invention. However, it will be clear to those skilled in the art that similar results are obtained with the complex of the present invention as with the disseminative complex in these examples when "cells expressing genes deleted from among genes for disseminative capability in the RNA molecule contained in the complex" are used as host cells.

The present inventors have confirmed that, for the efficient reconstitution of Sendai virus particles, cDNA to be introduced into cells must be in the circular form rather than in the linear form, and, for viral particle formation at a high efficiency, the transcription of the positive strand RNA is preferred to that of the negative strand RNA within cells. Although these conditions may not necessarily be applicable to the reconstitution of all other negative strand RNA viruses, it is possible to search for appropriate conditions for the reconstitution of other negative strand RNA viruses based on the disclosure of the present invention and conventional technology, indicating a possibility for establishing techniques to produce basic materials of desired negative strand viral vectors, that is, the viral reconstitution systems.

Sendai virus reconstitution can be initiated following transfection with full-length viral RNA, either negative or positive sense, that has been synthesized in vitro from the cDNAs. This indicates that, if cells which express all viral proteins (N, P, and L) required for initial transcription, replication, and encapsidation are constituted, the recombinant Sendai virus, eventually complexes described above can be formed entirely without using helper viruses such as vaccinia virus. Since cells which express all the three viral proteins required for initial transcription, replication, and encapsication were already described [J. Virology, 68, 8413–8417 (1994)], those skilled in the art may form such complementing cells. The cell type described in said reference are the one derived from the 293 cell line which carries three of Sendai virus genes, namely NP, P, and L, on its chromosome, expressing proteins encoded by the three genes, NP, P, and L.

From numerous examples of viral vectors, if viral particles can be efficiently reconstructed from nucleic acids, it is obvious that those skilled in the art are able to readily exchange a desired viral gene, insert a foreign gene, or inactivate or delete a desired gene. For example, an article on the use of DI (defective interfering) particles [J. Virol., 68, 8413–8417 (1994)] clearly indicates that, when Sendai virus RNA devoid of most of the protein-conding region but intact in its promoter sequences at both termini can be replicated in cells, if group of enzymes (L and P proteins) necessary for transcription and replication and the structural protein N to encapsidate the viral RNA are provided simultaneously in the cells. Therefore, once an RNA molecule containing a foreign gene transcribed from "specific viral cDNA deficient in at least a part of structural genes but normal in genes coding for N, P, and L, begins to be replicated by N, P, and L coexpressed by the cotransfected plasmid cDNAs, a virus particle will be formed, which is infectious to and autonomously replicating in a new cell, but deficient in the disseminative potency, and can express the foreign gene. Such complexes are extremely useful as a vector for gene therapy. That is, in the present invention, with a negative strand RNA virus, it becomes possible to prepare complexes which are infectious as well as autonomously replicative to express a foreign gene but is deficient in the disseminative potency.

Such complexes defective in certain viral genes can be recovered and amplified from cells which express the corresponding (to the deleted genes) structural proteins to complement the defects of the recombinant virus genes. Taking embryonated avian eggs into consideration as the most suitable host for proliferating such a defective, recombinant Sendai virus to a high titer, it is considered that transgenic avians, their eggs and cells which carry at least one or more genes out of M, F and HN genes of Sendai virus on chromosome are suitable for amplifying the complexes. Methods for preparing transgenic avians have been reported [Poultry Sci., 65, 1445–1458 (1986); BioTechnology, 12, 60–63 (1994)], and those skilled in the art should appropriately produce transgenic birds carrying at least one or more genes out of M, F and HN genes on their chromosomes.

The present invention also provides a method for preparing the complex described above. In the following, cases related to Sendai virus are exemplified. Genome of Sendai virus Z is a single stranded RNA comprising 15384 nucleotides. Its entire base sequence has been determined from cDNA clones prepared by using reverse transcriptase [Nucleic Acids Research, 11, 7313–7330 (1983); Nucleic Acids Research, 12, 7965–7972 (1984); Nucleic Acids Research, 14, 1545–1563 (1986)]. Since its genome RNA is a negative strand, a group of enzymes and proteins are required to transcribe the genome. The newly made proteins (N, P, and L) from the primary transcripts replicate and encapsidate the nascent antigenomic RNA strand. This antigenome, in turn, is replicated to a new genome strand by the same N, P, and L proteins. At least six proteins including NP, P, M, F, HN, and L are known as proteins encoded by the genome RNA. It has been elucidated that, of these proteins, NP, P and L are factors essential and sufficient for replication [Journal of Virology, 68, 8413–8417 (1994)], and M, F and HN are components necessary for constructing the viral structure. Based on these facts, when a specific RNA virus from which RNA is derived is Sendai virus, it is possible to reconstruct an infectious complex by transferring both 1) cDNA transcribable to RNA and a gene encoding the RNA polymerase necessary for transcribing said RNA within cells or 2) an RNA molecule itself transcribed from said cDNA in vitro into cells wherein all the genes for the autonomous replication, NP, P, and L, and a group of genes, out of M, F and HN genes, that had been deleted to restrict cell to cell dissemination, are expressed. In this case, all these transacting genes, NP, P, L, M, F, and HN, may be transiently expressed by transfecting cells with the plasmids coding for the respective genes. However, genes related to disseminative capability at least are preferably incorporated into cellular chromosomes to be stably expressed.

The complex reconstituted as above can be produced to a high titer, by infecting cells which express genes, one or some of M, F, and HN genes, which had been deleted in the recombinant virus. Transgenic avian eggs expressing said group of genes are preferable for this purpose to produce the complex in a large scale.

In addition, M, F, and HN genes expressed in cells and animals are not necessarily of the wild-type Sendai virus. Any of those with functions equivalent to those of the wild-type will be usable. That is, any gene may be used where said gene has complementarity to the function of Sendai virus gene deleted to make the virus nondeseminating. Preferable cells to be used are host cells for Sendai virus. Any cells can be theoritically used, if they are sufficiently susceptible to and permissive for Sendai virus infection and replication, to express M, F, and/or HN genes, and complement the defect of the recombinant Sendai virus intracellularly produced.

Hitherto only the enhancement of expression efficiency has been emphasized with conventional RNA virus vectors, and little efforts have been made for developing compounds to suppress the RNA replication to prevent unfavorable results due to excessive expression.

As the "RNA replication inhibitor" of the present invention, any drugs to inhibit RNA-dependent RNA replication may be applied, and, for example, Ribavirin, TJ13025, etc. are used. Such replication inhibitors are effective, for example, when health deterioration is noticed with the cellular amplification of recombinant RNA, or when the down-regulation of intracellular expression of foreign genes derived from recombinant RNA is required.

As an embodiment of the present invention, processes for reconstituting the complex of the present invention from cDNA with the M gene deleted of Sendai virus (steps A–B), and those for amplifying said complex (steps B–C) are shown in FIG. 1.

In the following, the present invention will be concretely described with reference to Examples, but not be limited to them.

Figure 2:
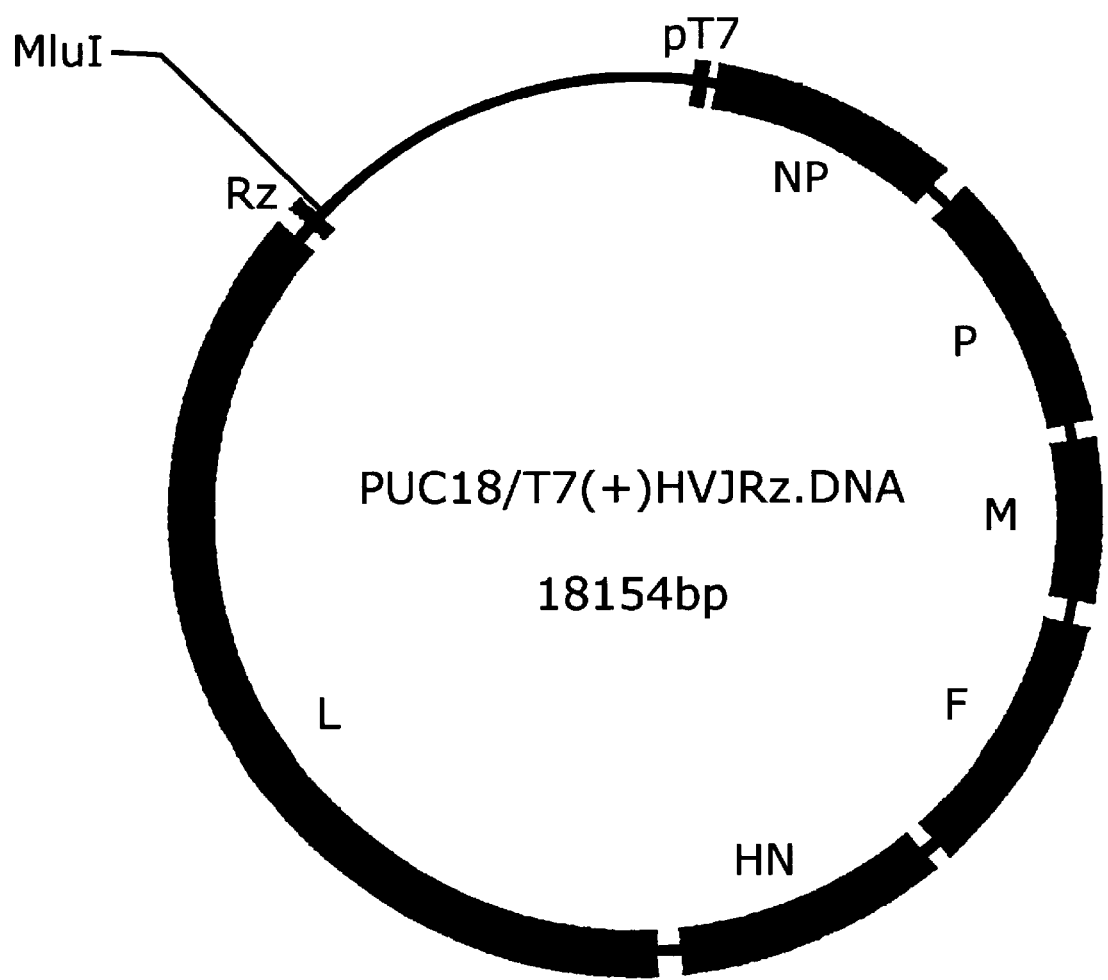
FIG. 2 is a schematic representation of the construction of a pUC18/T7(+) HVJRz.DNA.
Figure 3:
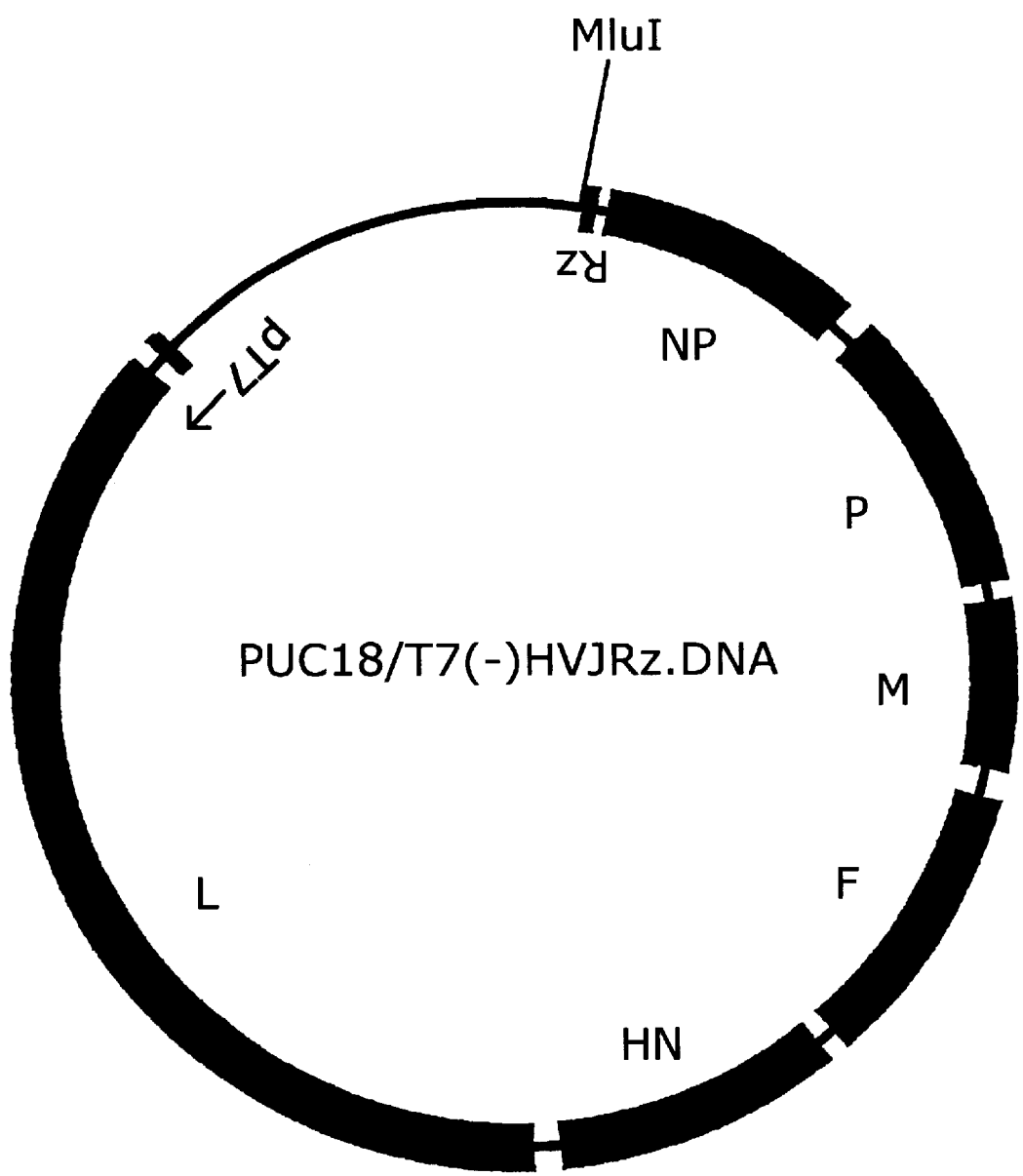
FIG. 3 is a schematic representation of the construction of a pUC18/T7(–) HVJRz.DNA.

EXAMPLE 1
Preparation of Sendai Virus cDNA Plasmids pUC18/T7(−) HVJRz.DNA and pUC18/T7(+) HVJRz.DNA Plasmid pUC18/T7(−) HVJRz.DNA was constructed by inserting a DNA molecule comprising T7 RNA polymerase promotor, Sendai virus cDNA designed to be transcribed to the negative strand RNA and the ribozyme gene in this order into pUC18 vector. Also, plasmid pUC18/T7(+) HVJRz.DNA was constructed by inserting a DNA molecule comprising T7 RNA polymerase promotor, Sendai virus cDNA designed to be transcribed to the positive strand RNA and the ribozyme gene in this order into pUC18 vector. Constructions of pUC18/T7(−) HVJRz.DNA and pUC18/T7(+) HVJRz.DNA are shown in FIGS. 2 and 3, respectively.

EXAMPLE 2
Reconstitution Experiment of Sendai Virus from cDNA

LLC-MK2 cells ($2\times10^6$) trypsinized in a usual manner were placed in a 60-mm diameter plastic dish, and incubated in MEM medium (MEM supplemented with 10% FBS) (10 ml) in a 5% $CO_2$ atmosphere at 37° C. for 24 h. After removing the medium and washing with PBS (1 ml), a suspension of recombinant vaccinia virus vTF7-3 expressing T7 polymerase in PBS (0.1 ml) was added to the cells at the multiplicity of infection (moi) of 2. The dish was gently agitated every 15 min to thoroughly spread the viral solution for 1 h infection. After removing the viral solution and washing with PBS (1 ml), a medium containing cDNA, which was prepared as follows, was added to the dish.

Nucleic acids shown in Tables 1 and 2 (containing plasmids expressing factors required for the replication of Sendai virus, pGEM-L, pGEM-P, and pGEM-NP, were placed in a 1.5-ml sampling tube, and adjusted to a total volume of 0.1 ml with HBS (Hepes buffered saline; 20 mM Hepes pH 7.4 containing 150 mM NaCl). In those tables, (−) and (+) cDNAs represent plasmids pUC18/T7(−) HVJRz.DNA and pUC18/T7(+) HVJRz. DNA, respectively, and /C and /L indicate that cDNA is introduced into cells in the circular form and linear form after digestion of those two plasmids with restriction enzyme MluI, respectively.

On the other hand, in a polystyrene tube were placed HBS (0.07 ml), DOTAP (Boehringer Mannheim) (0.03 ml). To this tube was added the nucleic acid solution described above, and the mixture was left standing as such for 10 min. Then, to this mixture was added the cell culture medium described above (2 ml, MEM supplemented with 10% FBS) followed by the vaccinia virus inhibitors, rifampicin and cytosine arabinoside C (C/Ara/C), to the final concentrations of 0.1 mg/ml and 0.04 mg/ml, respectively, resulting in the preparation of the medium containing cDNA described above.

The dish described above was incubated in a 5% $CO_2$ atmosphere at 37° C. for 40 h. The cells in the dish were harvested using a rubber policeman, transferred to an Eppendorf tube, sedimented by centrifuging at 6,000 rpm for 5 min, and re-suspended in PBS (1 ml). Aliquots of this cell suspension, as such or after diluted, were inoculated to 10-days old developing embryonated chicken eggs. That is, the cell suspension was diluted with PBS to the cell numbers shown in Table 1, and eggs inoculated with its 0.1 to 0.5-ml aliquots were incubated at 35° C. for 72 h, then at 4° C. overnight. Chorio-allantoic fluid was recovered as the source of reconstituted virus from these eggs using a syringe with a needle.

Hemagglutinin unit (HAU) and plaque forming unit (PFU) of the recovered virus solution were assayed as follows.

HAU was determined as follows. Chicken blood was centrifuged at 400× g for 10 min and the supernatant was discarded. Precipitates thus obtained were suspended in 100 volumes of PBS (−), and centrifuged at 400× g for 10 min to discard the supernatant. This procedure was repeated twice to prepare an 0.1% blood cell solution in PBS. Two-fold serial dilutions of virus solutions were prepared, and 0.05 ml each dilution to be assayed was dispensed into each well of 96-well titer plate. The blood cell solution (0.05 ml each) was further added to each well, gently swirled to ensure a thorough mixing, and left at 4° C. for 40 min. The reciprocals of the highest virus dilution to cause the hemagglutination observable with the naked eye was taken as HAU.

PFU was assayed as follows. CV-1 cells were grown to a monolayer on a 6-well culture plate. After the culture medium was discarded, a virus solution 10-fold serially diluted (0.1 ml each) was dispensed into each well of the culture plate to infect the cells at 37° C. for 1 h. During the infection, a mixture of 2× MEM free of serum and melted 2% agar (55° C.) was prepared, and trypsin was added to the mixture to a final concentration of 0.0075 mg/ml. After 1 h infection and removal of the virus solution, the culture medium mixed with agar (3 ml each) was added to each well of the culture plate, and incubated under a 5% $CO_2$ atmosphere at 37° C. for 3 days. Phenol red (0.1%) (0.2 ml) was added to each well, incubated at 37° C. for 3 h, and then removed. Unstained plaques were counted to estimate the virus titer as PFU/ml.

Table 1 shows Sendai virus template cDNAs transfected into LLC-2 cells, amounts of cDNA factors, pGEM-L, pGEM-P, and PGEM-NP, required for the RNA replication, incubation time, cell numbers inoculated to chicken eggs, HAU and PFU values recovered into the allantoic fluid.

form. The coexisting vaccinia virus in an amount of ca $10^4$ PFU/ml in the allantoic fluid was readily eliminated by the virus once again in eggs at a dilution of $10^{-7}$ or $10^{-8}$. This limiting dilution protocol was used to prepare vaccinia-free stock of recovered Sendai virus in this and all subsequent studies.

EXAMPLE 3

Survey of RNA Replication Factors Required for Sendai Virus Reconstitution

Experiments were performed to examine whether all three plasmids expressing the L, P, and NP proteins were required

TABLE 1

| Template cDNA | amount ($\mu$g) | pGEM -L ($\mu$g) | pGEM -P ($\mu$g) | pGEM -NP ($\mu$g) | Incubation time (h) | Amount of cells | HAU | PFU |
|---|---|---|---|---|---|---|---|---|
| (+)cDNA/C | 10 | 4 | 2 | 4 | 40 | $1.00 \times 10^5$ | 512 | $2 \times 10^9$ |
| (+)cDNA/C | 10 | 4 | 2 | 4 | 40 | $1.00 \times 10^5$ | 256 | $9 \times 10^8$ |
| (+)cDNA/C | 10 | 4 | 2 | 4 | 40 | $1.00 \times 10^6$ | 256 | $9 \times 10^8$ |
| (+)cDNA/L | 10 | 4 | 2 | 4 | 40 | $1.00 \times 10^5$ | <2 | <10 |
| (+)cDNA/L | 10 | 4 | 2 | 4 | 40 | $1.00 \times 10^5$ | <2 | <10 |
| (+)cDNA/L | 10 | 4 | 2 | 4 | 40 | $1.00 \times 10^6$ | <2 | <10 |
| (−)cDNA/L | 10 | 4 | 2 | 4 | 40 | $1.00 \times 10^4$ | <2 | <10 |
| (−)cDNA/L | 10 | 4 | 2 | 4 | 40 | $1.00 \times 10^5$ | <2 | <10 |
| (−)cDNA/L | 10 | 4 | 2 | 4 | 40 | $1.00 \times 10^6$ | <2 | <10 |
| (−)cDNA/C | 10 | 4 | 2 | 4 | 40 | $1.00 \times 10^4$ | <2 | <10 |
| (−)cDNA/C | 10 | 4 | 2 | 4 | 40 | $1.00 \times 10^5$ | <2 | <10 |
| (−)cDNA/C | 10 | 4 | 2 | 4 | 40 | $1.00 \times 10^6$ | 4 | $8 \times 10^3$ |

Samples showing both HAU and PFU were sedimented by ultra-centrifugation, re-suspended, purified by a sucrose density gradient centrifugation from 20% to 60%. The viral proteins of thus purified virions were fractionated by 12.5% SDS-PAGE. Each viral protein recovered from cDNAs samples was the same in size as that of the conventional Sendai virus.

These results demonstrated that Sendai virus can be reconstituted by introducing cDNAs into cells, and that virus particles are more efficiently reconstituted by introducing cDNAS transcribing positive strand RNAs as compared with those transcribing negative strand RNAs, and further by introducing cDNAs in the circular form rather in the linear for the reconstitution of Sendai virus. Experimental methods were similar to those described in Example 2 except that any combinations of two out of PGEM-L, pGEM-P, and PGEM-NP plasmids or only one out of them, instead of all these three combined as in Example 2, were introduced together with a template cDNA into cells.

Table 2 shows Sendai virus template cDNAs introduced into LLC-MK2 cells, amounts of the cDNA plasmids required for RNA replication in trans, incubation time, number of cells inoculated into chicken eggs, and values of HAU and PFU.

TABLE 2

| Template cDNA | amount ($\mu$g) | pGEM -L | pGEM -P | pGEM -NP | Incubation time (h) | Number of cells inoculated | HAU | PFU |
|---|---|---|---|---|---|---|---|---|
| (+)cDNA/C | 10 | 4 | 2 | 4 | 40 | $1.00 \times 10^5$ | 256 | $6 \times 10^8$ |
| (+)cDNA/C | 10 | 4 | 2 | 4 | 40 | $1.00 \times 10^6$ | 512 | $4 \times 10^9$ |
| (+)cDNA/C | 10 | 0 | 2 | 4 | 40 | $1.00 \times 10^6$ | <2 | <10 |
| (+)cDNA/C | 10 | 0 | 2 | 4 | 40 | $1.00 \times 10^6$ | <2 | <10 |
| (+)cDNA/C | 10 | 4 | 0 | 4 | 40 | $1.00 \times 10^6$ | <2 | <10 |
| (+)cDNA/C | 10 | 4 | 0 | 4 | 40 | $1.00 \times 10^6$ | <2 | <10 |
| (+)cDNA/C | 10 | 4 | 2 | 0 | 40 | $1.00 \times 10^6$ | <2 | <10 |
| (+)cDNA/C | 10 | 4 | 2 | 0 | 40 | $1.00 \times 10^6$ | <2 | <10 |
| (+)cDNA/C | 10 | 0 | 0 | 4 | 40 | $1.00 \times 10^6$ | <2 | <10 |
| (+)cDNA | 10 | 0 | 0 | 4 | 40 | $1.00 \times 10^6$ | <2 | <10 |
| (+)cDNA/C | 10 | 0 | 2 | 0 | 40 | $1.00 \times 10^6$ | <2 | <10 |
| (+)cDNA/c | 10 | 0 | 2 | 0 | 40 | $1.00 \times 10^6$ | <2 | <10 |
| (+)cDNA/C | 10 | 4 | 0 | 0 | 40 | $1.00 \times 10^6$ | <2 | <10 |
| (+)cDNA/C | 10 | 4 | 0 | 0 | 40 | $1.00 \times 10^6$ | <2 | <10 |

As shown in Table 2, no virus reconstitution was observed by introducing any combinations of two out of these three factors into cells, confirming the necessity of all three proteins L, P, and NP for the virus reconstitution.

EXAMPLE 4
Reconstitution Experiment of Sendai Virus in Vitro from Transcribed RNAs Since the reconstitution of Sendai virus from the functional cDNA clones was described in Example 2, it was further examined whether transcription products of said cDNAs in vitro, that is, v or (−) RNA and c or (+) RNA, can initiate and support similar reconstitution.

After the Sendai virus cDNA plasmids, pUC18/T7(−) HVJRz.DNA and pUC18/T7(+) HVJRz.DNA, were linearized with restriction enzyme MluI, using these DNAs as templates, RNA synthesis was performed in vitro with a purified T7 polymerase preparation (EPICENTRE TECHNOLOGIES: Ampliscribe T7 Transcription Kit). The method for synthesizing in vitro RNAs essentially followed the protocols provided with the kit. Using RNA products thus obtained in place of cDNAs in Example 2, similar experiments were performed, and the virus production was estimated by HA test. Results are shown in Table 3.

coli cells were transformed with this recombinant plasmid. DNAs were extracted from each colony of E. coli by the "Miniprep" method, digested with DraIII, and then electrophoresed. Positive clones (designated "clone 9" hereafter) were selected by confirming to contain DNA fragments of the size expected from the insertion. After DNA fragments were confirmed to have the authentic nucleotide sequence, DNAs were purified by a cesium chloride density gradient centrifugation. pSeV18+ inserted with the gp120 gene is designated "pSeVgp120" hereafter.

2. Reconstitution of Sendai virus containing pSevgp120 (Sevgp120) and analysis of gp120 expression Reconstitution of the virus from pSevgp120 in LLCMK2 cells, the virus recovery from allantoic fluid of embryonated chicken eggs, and assay of the viral HAU were done exactly as described in Example 2. The recovered virus was also examined for the expression of gp120 by ELISA as follows.

Samples (100 μl each allantoic fluid) were dispensed into each well of a 96-well plate which had been coated with monoclonal antibody against HIV-1, and incubated at 37° C. for 60 min. After washing with PBS, HRP-linked anti-HIV-1 antibody (100 μl each) was added to each well, and incubated at 37° C. for 60 min. After washing with PBS, tetramethylbenzidine was added to each well, and amounts of reaction product converted by the action of HRP under

TABLE 3

| Template cDNA | amount (μg) | pGEM-L (μg) | pGEM-P (μg) | pGEM-NP (μg) | Incubation time (h) | Number of cells inoculated | HAU | PFU |
|---|---|---|---|---|---|---|---|---|
| in vitro (−)RNA | 10 | 4 | 2 | 4 | 40 | $1.00 \times 10^6$ | 512 | $2 \times 10^9$ |
| in vitro (−)RNA | 10 | 4 | 2 | 4 | 40 | $1.00 \times 10^6$ | 512 | ND |
| in vitro (+)RNA | 10 | 4 | 2 | 4 | 40 | $1.00 \times 10^6$ | 2 | $5 \times 10^3$ |
| in vitro (+)RNA | 10 | 4 | 2 | 4 | 40 | $1.00 \times 10^6$ | <2 | ND |

These results indicate that virus can be reconstituted by introducing either negative or positive sense strand RNAs into cells.

EXAMPLE 5
Expression of Foreign Genes Inserted into Sendai Viral Vectors in Host Cells 1. Preparation of Sendai virus vector "pSeVgp120" inserted with a foreign gene, the gp120 of human immunodeficiency virus type 2 (HIV)

Using a set of primers comprising primer a (5'-TGCGGCCGCCGTACGGTGGCAATGAGTGAAGGAGAAGT-3')  (SEQ ID NO:1) and primer d (5'-TTGCGCCCGCGATGAACTTTCACCCTAAGTTTTTTATTACTACGGCG  (SEQ ID NO:2);
TACGTCATCTTTTTTCTCTCTGC-3')

the HIV-1gp120 gene was amplified on "pN1432" or a full-length cDNA of HIV-1 strain NL43 by the standard PCR techniques. PCR products were subjected to TA cloning, digested with NotI, and then inserted into the NotI site of "pSeV18+". pSeV18+ contains an additional 18 nucleotide sequence with a unique NotI restriction site which is placed before the ORF of NP gene of pUC/T7(+) HVJRz. Then, E.

acidic conditions were determined by following the optical density at 450 nm to estimate the expression amount of gp120. Results are shown in the left-hand column in Table 4.

The virus solution thus obtained was inoculated to CV-1 cells, and similarly examined for gp120 expression as follows. CV-1 cells were dispensed to a culture plate at 5×10^5 cells/plate, grown, and then the culture medium was discarded. After washing with PBS (−), the viral solution was added to the cells at the multiplicity of infection of 10, and incubated at 37° C. for 1 h. After the virus solution was discarded, washed with PBS (−), a plain MEM medium (MEM medium supplemented with antibiotics AraC and Rif, and trypsin) was added to the cells, and incubated at 37° C. for 48 h. After the reaction, the medium was recovered and assayed for HAU (by a similar method as described in Example 2) and examined for the expression of gp120 (by ELISA). Results are shown in the center column of Table 4. In addition, the supernatant of CV-1 cell culture medium was inoculated to embryonated chicken eggs again, and the virus solution thus obtained was assayed for HAU and also examined for the gp120 expression (by ELISA). Results are shown in the right hand column of Table 4.

TABLE 4

| | (µg/ml) | |
| --- | --- | --- |
| Allantoic fluid (F1) gp120 (HAU) | CV-1 medium (F1) gp120 (HAU) | Allantoic fluid (F2) gp120 (HAU) |
| 0.10 (4) | 3.46 (128) | |
| 0.15 (32) | 1.81 (128) | 1.56, 1.21 (512, 512) |
| 0.05 (32) | 2.20 (128) | |

As shown in Table 4, markedly high concentrations of gp120 were detected in CV-1 cells in culture (center column of the Table), and also in the allantoic fluids from embryonated chicken eggs inoculated again with the virus (right-hand column of the Table). In the left-hand and center columns of the Table are shown the mean values of three clones.

Furthermore, the expression of gp120 was analyzed by Western blotting. After the culture medium of CV-1 cells infected with Sevgp120 was centrifuged at 20,000 rpm for 1 h to sediment virus, the supernatant was treated with either TCA (10%, v/v) for 15 min on ice or 70% ethanol at −20° C., and centrifuged at 15,000 rpm for 15 min. Proteins thus precipitated were solved in an "SDS-PAGE sample buffer" (Daiichi Chemicals) at 90° C. for 3 min, and then subjected to electrophoresis on 10% SDS-polyacrylamide gel (SDS-PAGE). Proteins thus fractionated were transferred to PVDF membranes (Daiichi Chemicals), reacted with monoclonal antibody 902 at room temperature for 1 h, and then washed with T-TBS. The membranes were reacted with anti-mIgG (Amersham) at room temperature for 1 h, and washed with T-TBS. The membranes were then reacted with HRP-linked protein A (Amersham) at room temperature for 1 h, washed with T-TBS, and 4-chloro-1-naphthol (4CNPlus) (Daiichi Chemicals) was added to detect gp120. As a result, protein bands were visualized at positions corresponding to the expected molecular weight of gp120.

Figure 4:
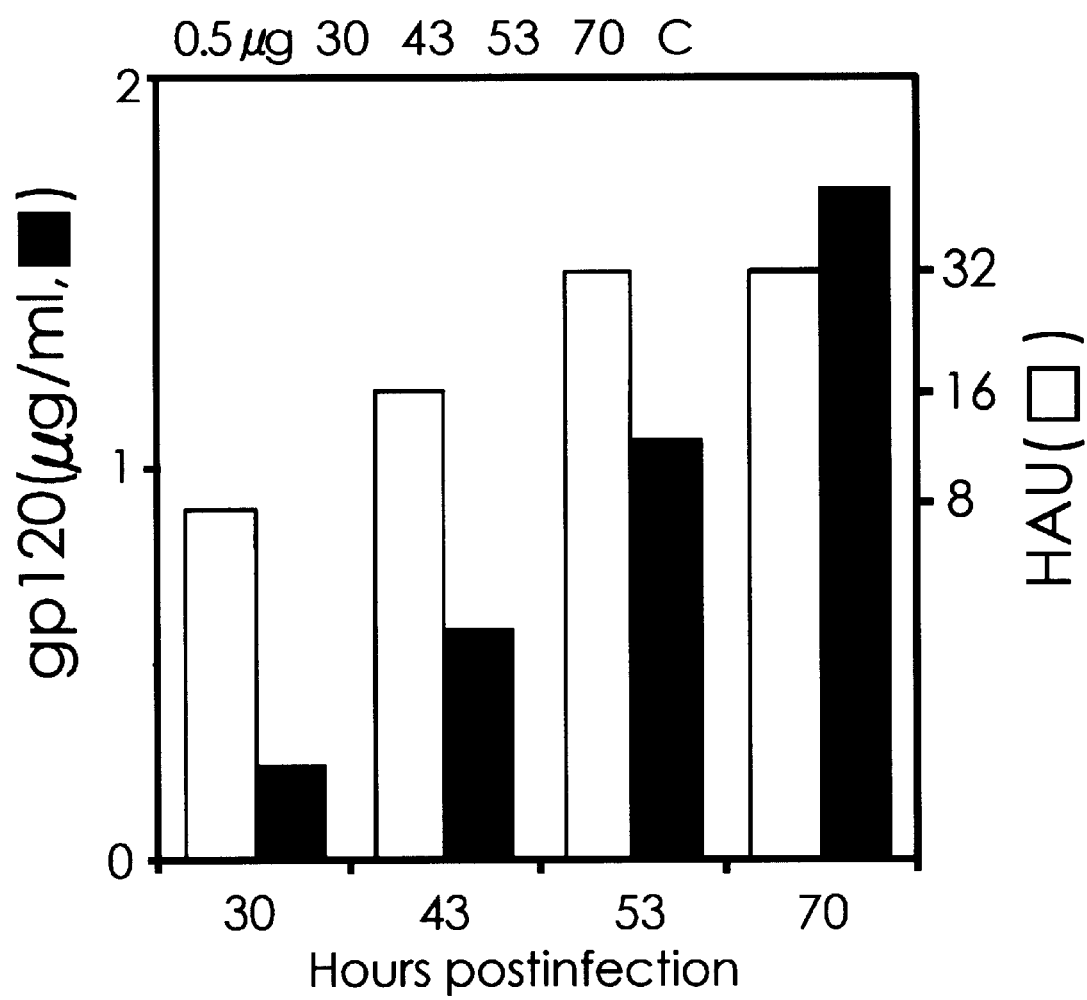
FIG. 4 is a graphical representation showing the relationship between the time after the infection of Sevgp120 into CV-1 cells and levels of HAU and gp120 expression.

In addition, effects of postinfection time of CV-1 cells transfected with SeVgp120 on the HAU value and gp120 expression amount were analyzed. CV-1 cells ($5\times10^6$) dispensed to 10-cm plate were infected with Sevgp120 at the multiplicity of infection of 10, and the culture medium (1 ml each) was postinfectionally recovered at 30, 43, 53 and 70 h, mixed with an equal volume of the fresh medium, and subjected to HAU assay, gp120 expression examination (by ELISA) and Western blotting. Results are shown in FIG. 4. As clearly shown in FIG. 3, the production of gp120 tends to increase with the increasing HA titer of Sendai virus.

EXAMPLE 6

Analyses of Sevgp120 Propagation and gp120 Production in Various Types of Cells

Using similar methods as those in Example 5 except for the use of various types of cells, HAU and gp120 expression levels (by ELISA) were assayed. Results are shown in Table

TABLE 5

| Cell type | Hours (postinfection) | HAU | rgp120 (µg/ml) |
| --- | --- | --- | --- |
| CV-1 | 96 | 32 | 2.5 |
| LLCMK2 | 48 | 16 | 0.5 |
| CHO | 55 | 4 | 0.46 |
| NIH3T3 | 48 | 4 | 0.25 |
| MT4 | 24 | 16 | 0.8 |
| MOLT4/ | 24 | 16 | 1.2 |

In the left-hand column of the Table are shown the postinfection times (hours) of various types of cells transfected with SeVgp120. As a result, SeVgp120 propagation and gp120 expression were detected in all types of cells tested.

EXAMPLE 7

Studies on the Expression of Luciferase Gene Inserted into the Sendai Viral Vector in Host Cells In order to isolate the luciferase gene for inserting to vectors, the luciferase gene bounded by the engineered NotI sites on both termini was constructed by the standard PCR using a set of primers

[5'-AAGCGGCCGCCAAAGTTCACGATGGAAGAC-3')        (30mer) (SEQ ID NO: 3)] and

[5'-TGCGGCCGCGATGAACTTTCACCC-        (69mer) (SEQ ID NO: 4)
TAAGTTTTTCTTACTACGGATTATTACAATTTGGACTTTCCGCCC-3' with the minigenome encoding plasmid, "pHvluciRT4", as a template. The PCR product was cloned into the NotI window of pSeV18⁺ to obtain a recombinant Sendai virus vector to which the luciferase gene is inserted. Then, this recombinant vector was transfected into LLCMK2 cells, and after 3 cycles of freezing and thawing, the cells were inoculated into embryonated chicken eggs. Chorio-allantoic membranes of developing eggs were excised out, twice washed with cold PBS (−), and, after the addition of lysis buffer (Picagene WAKO) (25 µl) and thorough mixing, centrifuged at 15,000 rpm for 2 min. To the supernatant (5 µl each) was added the substrate (IATRON) (50 µl), and the mixture was dispensed into each well of a 96-well plate. Fluorescent intensity was measured with a luminometer (Luminous CT-9000D, DIA-IATRON), and the enzyme activity was expressed as counts per second (CPS). As a result, an extremely high luciferase activity was detected. The egg grown recombinant virus was purified by passaging once again in eggs, so that the stock virus did not contain helper vaccinia virus. This stock virus was then used to infect CV-1 cells and examine luciferase expression in these cells. As shown in Table 6, again, extremely high luciferase activity was detected for infected CV-1 cells at 24-h postinfection (Table 6). In these experiments, Sendai virus which did not carry the luciferase gene was used as control (represented by "SeV" in the table). Results obtained from two clones are shown in the table.

TABLE 6

| | Fluorescence intensity (counts/10 sec) | |
|---|---|---|
| | Chorio-allantoic membrane | CV-1 (24 h postinfection) |
| Luc/SeV | 669187 | |
| | 2891560 | 8707815 |
| SeV | 69 | 48 |
| | 23 | 49 |

In the present invention, a system has been established allowing the efficient rescue of viral particles from cDNAs of negative strand viruses, and also a method has been developed enabling the production and amplification of "complexes comprised of RNAs derived from disseminative specific negative strand RNA virus and viral structural components containing no nucleic acids so as to have the infectivity and autonomous RNA replicating capability but no disseminative potency". Since said complexes can replicate only within infected cells but not spread from cell to cell, these techniques are especially useful in the fields of gene therapy, etc. wherein therapeutical safety is highly appreciated.

What is claimed is:

1. A complex devoid of infectious helper virus, wherein said complex is produced by introducing into a cell:
   a Sendai virus RNA molecule comprising a foreign gene;
   wherein said RNA molecule is selected from a group consisting of an RNA molecule and a cRNA of said RNA molecule;
   wherein said RNA molecule has at least one gene associated with the disseminative capacity of Sendai virus deleted or inactivated such that the RNA molecule is rendered non-disseminative and wherein said at least one gene is selected from the list of M, F and HN; and
   Wherein said cell expresses viral structural components comprising Sendai viral proteins essential for autonomous replication of Sendai virus, wherein said Sendai viral proteins provide the protein encoded by said at least one gene deleted or inactivated in the RNA molecule so as to provide the complex with cell infectivity and autonomous replicating capabilities but without the ability to disseminate.

2. The complex of claim 1, wherein said Sendai viral proteins comprise NP and RNA polymerase proteins derived or isolated from Sendai virus.

3. The complex of claim 1, wherein said viral proteins comprise Sendai viral proteins NP, P. and L.

4. A packaging cell to which the complex of claim 1 can disseminate, wherein said packaging cell is a mammalian or avian cell wherein said packaging cell comprises the one or more genes associated with the disseminative capacity of the Sendai virus deleted or inactivated in said RNA molecule of said complex, wherein said packaging cell produces a dissemination deficient yet replication and infection competent Sendai virus particle comprising the foreign gene when said complex is introduced into said packaging cell.

5. The packaging cell of claim 4, wherein said packaging cell is selected from the group consisting of:
   i. a cell comprising at least one gene selected from the group consisting of Sendai virus genes M, F, and HN;
   ii. a cell comprising a Sendai virus M gene;
   iii. a cell comprising a Sendai virus genes M, NP, P, and L; and
   iv. a cell comprising a Sendai virus genes M, F, HN, NP, P. and L.

6. The packaging cell of claim 4, wherein said packaging cell is derived or isolated from an avian egg.

7. The packaging cell of claim 4, wherein said packaging cell is derived or isolated from a mammalian or avian cell.

8. A method for preparing a foreign protein, wherein said method comprises the steps of introducing the complex of claim 1 into the packaging cell of claim 4 and recovering the protein encoded by the foreign gene comprised in said RNA molecule.

9. A method for producing a dissemination deficient yet replication and infection competent Sendai viral particle comprising a foreign gene, wherein said method comprises the steps of introducing the complex of claim 1 into the packaging cell of claim 4.

10. The packaging cell of claim 4, wherein said packaging cell does not express a heterologous RNA polymerase.

11. The method of claim 9, wherein said packaging cell does not express a heterologous RNA polymerase.

* * * * *

UNITED STATES PATENT AND TRADEMARK OFFICE
CERTIFICATE OF CORRECTION

PATENT NO. : 6,723,532 B2  
DATED : April 20, 2004  
INVENTOR(S) : Nagai et al.

It is certified that error appears in the above-identified patent and that said Letters Patent is hereby corrected as shown below:

Title page,  
Item [73], Assignee, change assignee name from "Dnavec" to -- DNAVEC --.  
Item [63], please change the filing date of PCT/JP96/03068 from "Oct 22, 1995" to -- Oct. 22, 1996 --.  
Item [56], References Cited, OTHER PUBLICATIONS,  
"B. Gotoh et al.," reference, please change the word "ciral" to -- viral --.  
"M. Tashiro et al.," reference, please change the word "Importance" to -- involvement --.  
"P. Calain et al.," reference, please change the word "characterisation" to -- characterization --.  
"W. Willenbrink et al.," reference, please change the number "668" to -- 68 --.  
"A.P. Dubin et al.," reference, (2nd occurrence), please change the words "replicationof" to -- replication of --.  
"C.J. Buccholz et al.," reference, please change the word "caboxy" to -- carboxy --.  
Item [57], ABSTRACT,  
Line 3, please change the word "Production" to -- production --.

Column 23,  
Line 12, please change the word "Wherein" to -- wherein --.

Signed and Sealed this

Twenty-sixth Day of October, 2004

JON W. DUDAS  
*Director of the United States Patent and Trademark Office*